United States Patent
Lin

[11] Patent Number: 5,738,125
[45] Date of Patent: Apr. 14, 1998

[54] DENTAL FLOSSER

[76] Inventor: Jyh-Sheng Lin, 184, Ching-Yun Rd., Tuu-Cherng City, Taipei, Taiwan

[21] Appl. No.: 674,106

[22] Filed: Jul. 3, 1996

[51] Int. Cl.$^6$ .................................................. A61C 15/00
[52] U.S. Cl. ........................... 132/323; 132/321; 132/325
[58] Field of Search ................................. 132/321, 323, 132/324, 325, 326, 327; 242/405.1, 405.2; 248/175, 431, 435

[56] References Cited

U.S. PATENT DOCUMENTS

| 754,841 | 3/1904 | Bessonet | 132/325 |
|---|---|---|---|
| 4,041,962 | 8/1977 | Johansson et al. | 132/323 |
| 4,162,687 | 7/1979 | Lorch | 132/323 |
| 4,736,757 | 4/1988 | Badoux | 132/323 |
| 4,966,176 | 10/1990 | Lachenberg | 132/325 |
| 5,113,880 | 5/1992 | Honda et al. | 132/323 |
| 5,388,600 | 2/1995 | Hart | 132/323 |

Primary Examiner—Gene Mancene
Assistant Examiner—Pedro Philogene
Attorney, Agent, or Firm—Birch, Stewart, Kolasch & Birch, LLP

[57] ABSTRACT

A dental flosser including a holder and an operation end keeping a certain contact angle with the holder, and the operation end having a horizontal section on the front end, and floss mounted on the front edge of two ribs resembling an arch on the operation end so that the floss is kept perpendicular to the holder. The structure of such dental flosser makes it easy for stretching floss into the space of each tooth and closely touching the gum line. A firm and perpendicular thrust force and tension force may be formed upon the crown surface of the tooth space by pushing the holder forward or pulling it backward with the hand, with the stream of force in conjunction with moving dental flosser up and down made easier for the floss removing the dental plaque from the crown surface. Such an easy removal of dental plaque has even more significant effect for molars located deeper inside the mouth.

12 Claims, 4 Drawing Sheets

DENTAL FLOSSER

BACKGROUND OF THE INVENTION

The present invention relates to a dental flosser, and particularly to a dental flosser structure which is effective for applying force to clean up dental plaque in the molar area.

DESCRIPTION OF THE BACKGROUND ART

Among various organs of human body, the teeth have played a key role for chewing food and are also the upstream factory of the stomach, for delivering food after being crushed to the stomach for further digestion and absorption so as to provide nutrition as needed for the body. Because teeth are so important, the maintenance and care of them has become one of daily necessity items. Perhaps everyone has a fixed habit of brushing their teeth day and night but dentists still recommend us to rinse the mouth or brush teeth after each meal, and what is more important is to not forget using dental flosser for cleaning up dental plaque left between the teeth because these dental plaque that can not be removed by a tooth brush are the main cause of periodontal disease. With regard to the use of dental flosser, it is believed to be a strange issue for many people because a tooth brush is widely known and is the main and common tool for cleaning up the teeth. Many people do not use dental flosser until recommended by the dentists owing to suffering from dental disease. Though dental flosser has significant effect for removing dental plaque left between the teeth, however there are a number of obstacles for use. One obstacle is not getting used to it because of operation error and the other one is it not being available for operation among the public. Because of the problem of not being available for operation among the public, dental flosser is not so popular as toothpick. Referring to the problem of occasion for use, dental flosser developed thereafter has resolved it.

The dental flosser as mentioned above relates to a structure as shown in FIG. 1, comprising a floss 12 laid between an integrally molded holding end 10 and arch operation end 11. The length of such dental flosser is similar to that of a toothpick so it may be brought by the user for cleaning up the teeth after each meal. The user only needs to hold the dental flosser with one hand and to cover the mouth with the other hand so as to clean up the teeth easily among the public without worry about impolite manners for exposing the teeth during the use of the dental flosser.

Though the appearance of dental flosser has resolved the problems relating to difficult use of floss and limited occasions to use, however such dental flosser has caused other problems of use such as the condition in FIG. 2. When the dental flosser 1 is used for cleaning up the space between the incisor area 20 and the canine tooth area 21, and the axial center line 22 of tooth arch is governed, and lateral angle (O) adjustment of open mouth shall not exceed 70 degrees and it is stretched into the space 23 between the teeth within the scope of the open mouth for cleaning up the dental plaque by moving up and down closely touching the crown surface 24. For the removal of tartar from the space between the incisor area 20 and the canine tooth area 21, because dental flosser is obliquely stretched from the mouth to keep parallel with the space between the teeth so it can be convenient for applying force to remove the tartar without any problem; however, for the molar area 25 on the rear part, the removal of dental plaque is apparent to have difficulty and reasons lie in: the maximum open mouth may be accessible only to the first molar 251 or second molar 252 of right/left molar area 25, and the operation of dental flosser 1 within such a limited open angle 26 has good control without limit by the mouth opening because only operation end 11 is moving in the mouth whole holding end 10 stays outside the mouth; nevertheless, for the second molar 252 and third molar 253 part, because the floss on operation end 11 is nearly perpendical to the space 23 between the teeth when dental flosser is stretched into the mouth, both opertion end 11 and holding end 10 are located within the mouth so it is difficult for adjusting dental flosser to adapt to the direction of the space between the teeth. Even if the best effort were made to open the mouth to the maximum or the dental flosser were stretched into the deeper part of the mouth, the dental flosser could only be kept at a certain contact angle with the space rather than to make a perfect match between them. Therefore not only the floss on operation end can not be stretched into the space between the teeth but also dental plaque removal may become difficult even if the floss were flexible enough for stretching into the space between the teeth owing to certain contact angle between holding end of dental flosser and the space and limited space in the mouth.

A newer type of dental flosser as shown in FIG. 3 has appeared in response to the defect of conventional dental flosser for removing dental plaque of molar. The dental flosser has a downward extending operation end 31 with floss 32 perpendicular to holder 30. With the help of floss perpendicular to holder, keeping holder 30 outside the mouth while stretching operation end 31 into the mouth can make stretching floss 32 into the space between the molars 25 easier to clean up the dental plaque up and down. Though the improved dental flosser 3 is effective to remove leftover on the space between the molars in an easy manner, however it has some defects relating to the use as a result of poor structural design. The defects include: the floss can not be stretched into the gum line of the space so it can not thoroughly clean up the dental plaque on the gum line; the second is holding control portion 301 of holder 30 which is not effective for applying force to remove the dental plaque. The cause of such defects lies in: contact angle between operation end 31 and holder 30 is not so designed as subject to the height and width of teeth; when the floss is not yet stretched to reach the bottom (gum line) of the space 23 between the teeth, holder 30 has touched the crown surface 24; if floss were desired for stretching deeper into the gum line 28, tail end of holder 30 has to be elevated to result in holder touching the crown surface on the other end (FIG. 4) and this would be an obstacle to removing the dental plaque up and down; further with regard to applying force of dental flosser to remove the dental plaque because the dental flosser depends on applying force from both sides of holding control portion 301 laterally held by fingers, the direction of force applied (arrow in FIG. 5A) is perpendicular to the direction of removing the dental plaque up and down by floss 32 (arrow of dotted line in FIG. 5B and removing the dental plaque from both sides of holding control portion 301 of holder held by fingers is not effective to remove the dental plaque and further holder 30 could break away from fingers if floss were excessively pushed onto the incisor ledge 27.

According to the aforesaid analysis, it is known whether the conventional floss, dental flosser or further improved dental flosser has more or less problems relating to the use or function. Therefore a new and improved dental flosser has been developed in response to the defects of the conventional floss and dental flosser, which has appropriate contact angle between holder and operation end and floss mounting end horizontally extending forward from operation end. With the help of said contact angle and horizontal floss mounting end, the floss can easily be stretched to reach the gum line for removing the dental plaque and may clean up the dental plaque by moving up and down easily without elevating the tail end of holder. The structure and function of the present invention will further be described below.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF PREFERRED EMBODIMENTS

Figure 1:
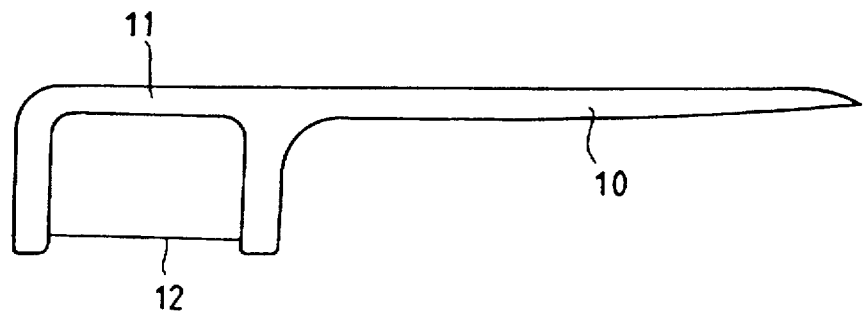
FIG. 1 is an outlook view of the conventional dental flosser.
Figure 2:
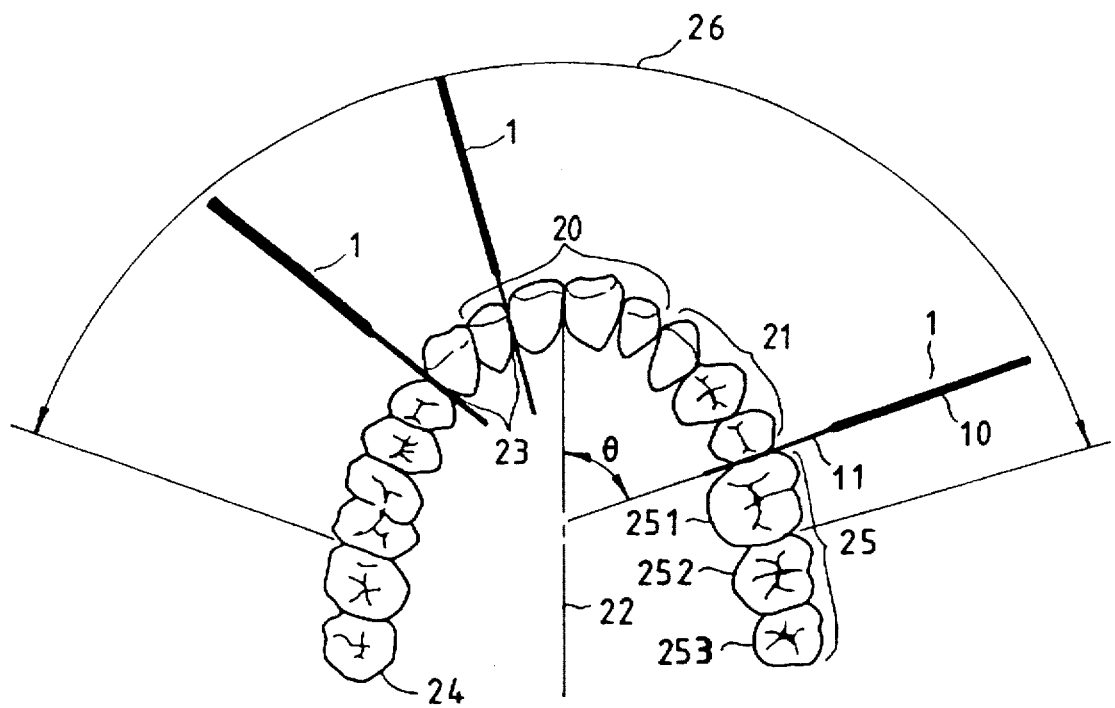
FIG. 2 is a schematic view illustrating the condition of the conventional dental flosser used on different parts of the teeth.
Figure 3:
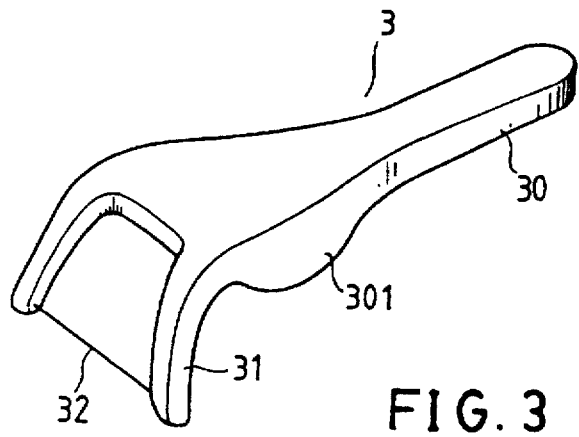
FIG. 3 Is an elevational view illustrating the structure of the improved dental flosser.
Figure 4:
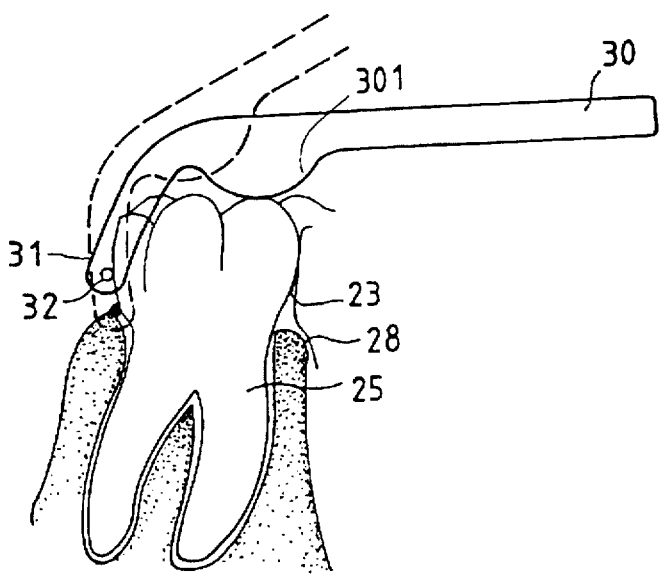
FIG. 4 s a schematic view illustrating the operation of improved dental flosser.
Figure 5A:
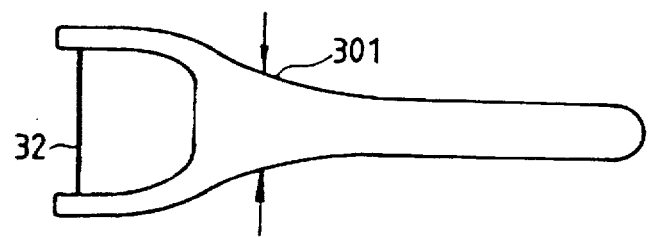
FIG. 5A is a plan schematic view illustrating the operation of improved dental flosser.
Figure 5B:
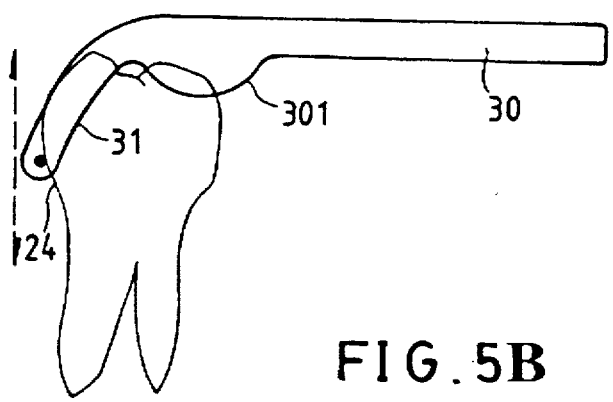
FIG. 5B is a side view of FIG. 5A.
Figure 6:
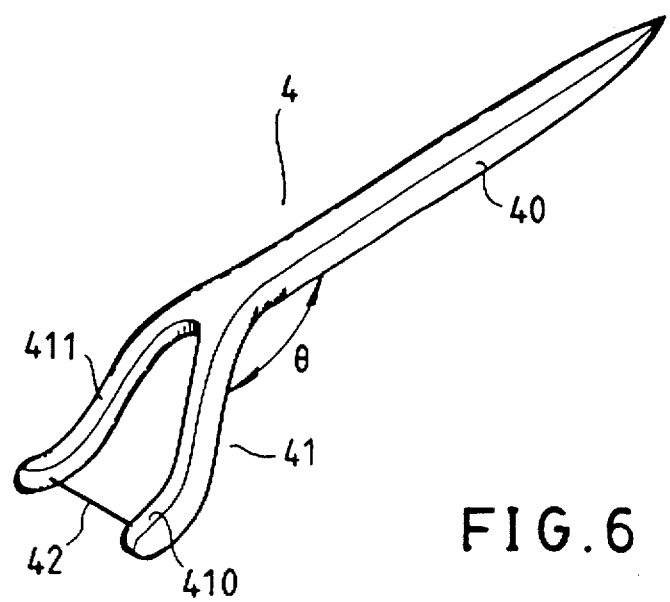
FIG. 6 is an elevational view showing a perspective view of the present invention.

Referring to FIG. 6, holder 40 and operation end 41 of the present invention keep contacted at certain angle and said angle (θ) is preferably around 150–170 degrees. The floss 42 mounting end in front of operation end 41 has a horizontal section 410 and floss 42 and holder 40 are perpendicular and mounted on an arch formed by two ribs 411 of operation end 41.

Figure 7:
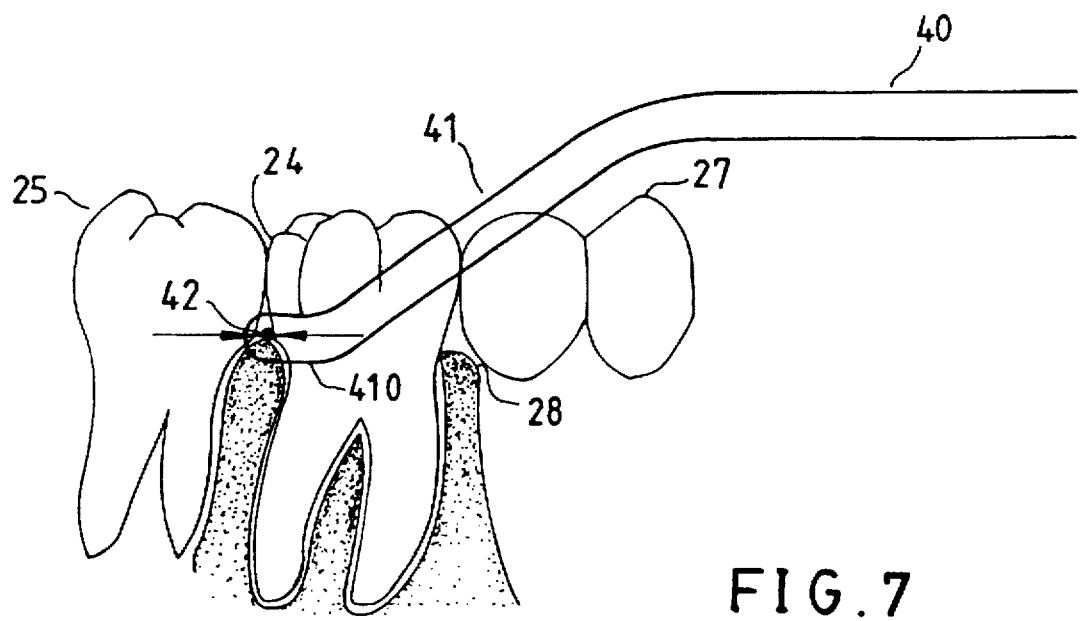
FIG. 7 is a schematic view illustrating the action of the present invention.

Referring to FIG. 7, oblique stretching operation end 41 and horizontal section 410 in front of operation end 41 which may stretch the floss 42 at most to reach the space between the teeth, and when floss 42 is placed deep into the gum line 28 without necessity of elevating tail end of holder 40 and holder 40 may keep a gap between incisor ledge 27 for finger to stretch inside. In FIG. 7, with perpendicular thrust force (as shown by the arrow) of floss 42 upon the crown surface 24 and the function of contact angle between holder 40 and operation end 41, it has become very firm. The user only needs to push the present invention forward or pull it backward from holder 40 a maximum perpendicular thrust force and tension force will be produced to act upon the crown surface, and match holding the upper and lower ends of intermediate section of holder 40 with the hand may move the present invention up and down on the crown surface for removing the dental plaque therefrom. The use of the present structure for removing the dental plaque from the space between molars represents to remove the dental plaque with lower force without the need of stretching dental flosser horizontally into the mouth, and operation obstacle may be avoided for holder will not touch the crown surface on the other side.

Figure 8:
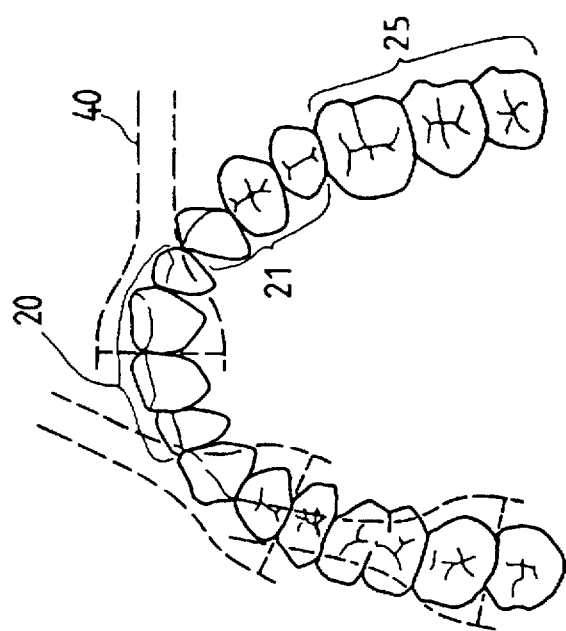
FIG. 8 is a schematic view illustrating the condition of the present invention used on different parts of the teeth.

Referring to FIG. 8, the present invention not only is very convenient for removing the dental plaque within molar area 25 but also has significant effect of removing the dental plaque within incisor area 20 and canine area 21. As seen in FIG. 8, there has no problem arising from operation because the dental flosser may be operated within incisor area 20 and canine area 21 when the mouth is open and holder 40 stays outside the mouth. The largest action force produced by special contact angle and operation end horizontally stretching forward according to the present invention makes it easy for removing the dental plaque from incisor and canine teeth.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

What is claimed is:

1. A dental flosser comprising:

a holder having an operation end, the operation end having a contact angle with the holder of preferably around 150 to 170 degrees, the holder having two ribs which form an arch to form the operation end of the holder, said operation end having a frontal horizontal section; and a floss mounted between said two ribs, the floss being perpendicular to said holder.

2. The dental flosser as claimed in claim 1, wherein the contact angle is between 150 to 170 degrees.

3. The dental flosser as claimed in claim 2, wherein the floss is permanently mounted to the two ribs.

4. The dental flosser as claimed in claim 3, wherein the two ribs with the frontal horizontal section have a uniform cross section along a length thereof.

5. The dental flosser as claimed in claim 4, wherein the holder has a longitudinally extending body portion, the two ribs extending from a forward end of the body portion and forming the contact angle with the body portion at a junction of the ribs with the body portion.

6. The dental flosser as claimed in claim 5, wherein the frontal horizontal section forms another angle with the two ribs.

7. The dental flosser as claimed in claim 3, wherein the holder has a longitudinally extending body portion having a longitudinal axis, the arch formed by the two ribs being inclined away from the longitudinal axis of the body portion in an area at a junction between the ribs and the body portion.

8. The dental flosser as claimed in claim 1, wherein the floss is permanently mounted to the two ribs.

9. The dental flosser as claimed in claim 1, wherein the two ribs with the frontal horizontal section have a uniform cross section along a length thereof.

10. The dental flosser as claimed in claim 1, wherein the holder has a longitudinally extending body portion, the two ribs extending from a forward end of the body portion and forming the contact angle with the body portion at a junction of the ribs with the body portion.

11. The dental flosser as claimed in claim 10, wherein the frontal horizontal section forms another angle with the two ribs.

12. The dental flosser as claimed in claim 1, wherein the holder has a longitudinally extending body portion having a longitudinal axis, the arch formed by the two ribs being inclined away from the longitudinal axis of the body portion in an area at a junction between the ribs and the body portion.

* * * * *